(12) United States Patent
Sievi et al.

(10) Patent No.: US 11,629,410 B2
(45) Date of Patent: Apr. 18, 2023

(54) PREPARATIONS OF PLATINUM COMPLEXES

(71) Applicant: Heraeus Deutschland GmbH & Co. KG, Hanau (DE)

(72) Inventors: Robert Sievi, Hanau (DE); Michael Gock, Hanau (DE); Richard Walter, Hanau (DE); Holger Ulland, Willich (DE)

(73) Assignee: HERAEUS DEUTSCHLAND GMBH & CO. KG, Hanau (DE)

( * ) Notice: Subject to any disclaimer, the term of this patent is extended or adjusted under 35 U.S.C. 154(b) by 0 days.

(21) Appl. No.: 17/755,571

(22) PCT Filed: Jul. 9, 2020

(86) PCT No.: PCT/EP2020/069375
§ 371 (c)(1),
(2) Date: May 2, 2022

(87) PCT Pub. No.: WO2021/089203
PCT Pub. Date: May 14, 2021

(65) Prior Publication Data
US 2022/0364238 A1 Nov. 17, 2022

(30) Foreign Application Priority Data
Nov. 6, 2019 (EP) .................................. 19207342

(51) Int. Cl.
*C23C 18/08* (2006.01)
*C07F 15/00* (2006.01)

(52) U.S. Cl.
CPC .......... *C23C 18/08* (2013.01); *C07F 15/0086* (2013.01)

(58) Field of Classification Search
CPC ............................ C07F 15/0086; C23C 18/08
See application file for complete search history.

(56) References Cited

U.S. PATENT DOCUMENTS

2003/0207568 A1* 11/2003 Byun ................... C23C 18/06
438/681

FOREIGN PATENT DOCUMENTS

| JP | H08157490 A | 6/1996 |
| JP | H1018036 A | 1/1998 |
| WO | 90/07561 A1 | 7/1990 |
| WO | 9210529 A1 | 6/1992 |
| WO | 2016044732 A1 | 3/2016 |
| WO | 2017035171 A1 | 3/2017 |

* cited by examiner

*Primary Examiner* — Robert A Vetere
(74) *Attorney, Agent, or Firm* — Blank Rome LLP

(57) ABSTRACT

Preparation containing:
(A) 30 to 90% by weight of at least one organic solvent;
(B) 10 to 70% by weight of at least one platinum complex of the type $[L1L2Pt[O(CO)R1]X]_n$,
wherein L1 and L2 represent the same or different monoolefin ligands, or together represent a compound L1L2 acting as a diolefin ligand,
wherein X is selected from bromide, chloride, iodide, and —O(CO)R2,
wherein —O(CO)R1 and —O(CO)R2 represent the same or different C6-C18 non-aromatic monocarboxylic acid groups, or together represent a C8-C18 non-aromatic dicarboxylic acid group —O(CO)R1 R2(CO)O—,
wherein they are mononuclear platinum complexes with n=1, or wherein, if L1L2 and/or —O(CO)R1 R2(CO)O— are present, they may be polynuclear platinum complexes with a whole number n>1, and
(C) 0 to 10% by weight of at least one additive.

16 Claims, No Drawings

PREPARATIONS OF PLATINUM COMPLEXES

The present invention relates to preparations of platinum complexes and to the use of the preparations for producing platinum layers on substrates.

WO90/07561 A1 discloses platinum complexes of the formula $LM[O(CO)R]_2$, wherein L represents a nitrogen-free cyclic polyolefin ligand, preferably cyclooctadiene (COD) or pentamethylcyclopentadiene, and M represents platinum or iridium, and wherein R represents benzyl, aryl, or alkyl having four or more carbon atoms, particularly preferably phenyl. The platinum complexes serve as fuel additives.

The object of the present invention was to find preparations which can be used to produce platinum layers on substrates, including temperature-sensitive substrates.

The object can be achieved by providing a preparation comprising or consisting of:
(A) 30 to 90% by weight (wt. %) of at least one organic solvent,
(B) 10 to 70% by weight of at least one platinum complex of the type $[L1L2Pt[O(CO)R1]X]_n$,
wherein L1 and L2 represent the same or different monoolefin ligands, or together represent a compound L1L2 acting as a diolefin ligand,
wherein X is selected from bromide, chloride, iodide, and —O(CO)R2,
wherein —O(CO)R1 and —O(CO)R2 represent the same or different C6-C18 or preferably C8-C18 non-aromatic monocarboxylic acid groups, or together represent a C8-C18 non-aromatic dicarboxylic acid group —O(CO)R1R2(CO)O—,
wherein they are mononuclear platinum complexes with n=1, or wherein, if L1L2 and/or —O(CO)R1R2(CO)O— are present, they may be polynuclear platinum complexes with a whole number n>1, and
(C) 0 to 10% by weight of at least one additive.

In a preferred embodiment, they are preparations in which the component (B) constituting 10 to 70% by weight is composed of at least one platinum complex of the type $[L1L2Pt[O(CO)R1]X]_n$,
wherein L1 and L2 together represent a compound L1L2 functioning as a diolefin ligand,
wherein X is selected from bromide, chloride, iodide, and —O(CO)R2,
wherein —O(CO)R1 and —O(CO)R2 represent the same or different C6-C18 or preferably C8-18 non-aromatic monocarboxylic acid groups, and
wherein they are mononuclear platinum complexes with n=1, or polynuclear platinum complexes with a whole number n>1. Here, L1L2 represents a compound acting as a diolefin ligand.

In the case of polynuclear platinum complexes, the number n generally represents a whole number, for example in the range of 2 to 5. In other words, whole number n>1 is generally in the range from 2 to 5; in particular, n is in this case equal to 2 and the platinum complexes are dinuclear platinum complexes. In particular, the compound L1L2 or, respectively, the dicarboxylic acid group —O(CO)R1R2 (CO)O— act as bridging ligands in the polynuclear platinum complexes. X can also have a bridging effect.

The platinum is present in the +2 oxidation state in the platinum complexes.

In the preparation according to the invention, component (B) is present dissolved in component (A). If the optional component (C) is present in the preparation according to the invention, this component (C) will also preferably be present dissolved in component (A). In other words, in the absence of the optional component (C), the preparation according to the invention is an organic solution, more precisely, a genuine, i.e., non-colloidal, organic solution; the same applies when the optional component (C) is present in the preferred form, i.e., in the form dissolved in component (A).

The preparation according to the invention contains 30 to 90% by weight of at least one organic solvent (A). The organic solvent(s) can be selected from a plurality of common organic solvents since the platinum complexes have good to unlimited solubility in such organic solvents. Expediently, the organic solvent(s) is/are substantially volatile under the processing conditions of the preparation according to the invention; this applies in particular to the stage after the preparation according to the invention has been applied to a substrate. In general, the boiling points of the organic solvent(s) are in the range of 50 to 200° C. or higher, for example 50 to 300° C. Examples of organic solvents (A) include aliphates and cycloaliphates, each having 6 to 12 carbon atoms; halocarbons, such as di-, tri-, and tetrachloromethane; aromatics; araliphates, such as toluene or xylene; alcohols, such as ethanol, n-propanol, and isopropanol; ethers; glycol ethers, such as mono-C1-C4 alkyl glycol ethers and di-C1-C4 alkyl glycol ethers, for example ethylene glycol mono-C1-C4 alkyl ether, ethylene glycol di-C1-C4 alkyl ether, diethylene glycol mono-C1-C4 alkyl ether, diethylene glycol di-C1-C4 alkyl ether, propylene glycol mono-C1-C4 alkyl ether, propylene glycol di-C1-C4 alkyl ether, dipropylene glycol mono-C1-C4 alkyl ether, and dipropylene glycol di-C1-C4 alkyl ether; esters having 2 to 12 carbon atoms; and ketones, such as acetone, methyl ethyl ketone, methyl isobutyl ketone, and cyclohexanone. Araliphates, such as toluene or xylene; alcohols, such as ethanol, n-propanol, and isopropanol; and glycol ethers, such as mono-C1-C4 alkyl glycol ethers and di-C1-C4 alkyl glycol ethers, for example ethylene glycol mono-C1-C4 alkyl ethers; ethylene glycol di-C1-C4 alkyl ether, diethylene glycol mono-C1-C4 alkyl ether, diethylene glycol di-C1-C4 alkyl ether, propylene glycol mono-C1-C4 alkyl ether, propylene glycol di-C1-C4 alkyl ether, dipropylene glycol mono-C1-C4 alkyl ether, and dipropylene glycol di-C1-C4 alkyl ether are preferred. Component (A) or the at least one organic solvent (A) consists particularly preferably of at least one alcohol, specifically at least one of the alcohols mentioned by way of example, and/or of at least one glycol ether, specifically at least one of the glycol ethers mentioned by way of example. Particularly preferred as component (A) are corresponding mixtures of 30 to 70% by weight alcohol and the remaining proportion by weight up to 100% by weight of glycol ether.

The preparation according to the invention contains 10 to 70% by weight of at least one platinum complex of the type $[L1L2Pt[O(CO)R1]X]_n$ (B). The platinum content of the preparation according to the invention originating from the at least one platinum complex can be, for example, in the range of 2.5 to 25% by weight.

In a first embodiment of mononuclear platinum complexes of the type L1L2Pt[O(CO)R1]X, L1 and L2 are the same or different monoolefin ligands; X represents bromide, chloride, iodide, or —O(CO)R2; and —O(CO)R1 and —O(CO)R2 are the same or different C6-C18 or preferably C8-C18 non-aromatic monocarboxylic acid groups with the respective exception of phenylacetic acid groups.

In a second and also preferred embodiment of mononuclear platinum complexes of the type L1L2Pt[O(CO)R1]X, L1 and L2 together are a compound L1L2 acting as a diolefin ligand at the same central platinum atom; X represents bromide, chloride, iodide, or —O(CO)R2; and —O(CO)R1 and —O(CO)R2 represent the same or different C6-C18 or preferably C8-C18 non-aromatic monocarboxylic acid groups, with the respective exception of phenylacetic acid groups.

In a third embodiment of mononuclear platinum complexes of the type L1L2Pt[O(CO)R1]X, L1 and L2 are the same or different monoolefin ligands; X represents —O(CO)R2; —O(CO)R1 and —O(CO)R2 together represent a C8-C18 non-aromatic dicarboxylic acid group —O(CO)R1R2(CO)O— acting as a bidentate ligand at the same central platinum atom.

In a fourth embodiment of mononuclear platinum complexes of the type L1L2Pt[O(CO)R1]X, L1 and L2 together are a compound L1L2 acting as a diolefin ligand at the same central platinum atom; X represents —O(CO)R2; and —O(CO)R1 and —O(CO)R2 together represent a C8-C18 non-aromatic dicarboxylic acid group —O(CO)R1R2(CO)O— acting as a bidentate ligand at the same central platinum atom.

In a first and also preferred embodiment of bi- or polynuclear platinum complexes of the type [L1L2Pt[O(CO)R1]X]$_n$, L1 and L2 together represent a compound L1L2 bridging different platinum centers and acting as a diolefin ligand; X represents bromide, chloride, iodide or —O(CO)R2; n represents 2, 3, 4 or 5, preferably 2; and —O(CO)R1 and —O(CO)R2 are the same or different C6-C18 or preferably C8-C18 non-aromatic monocarboxylic acid groups, in each case with the exception of phenylacetic acid groups.

In a second embodiment of bi- or polynuclear platinum complexes of the type [L1L2Pt[O(CO)R1]X]$_n$, L1 and L2 together represent a compound L1L2 bridging different platinum centers and acting as a diolefin ligand; X represents —O(CO)R2; n represents 2, 3, 4, or 5, preferably 2; and —O(CO)R1 and —O(CO)R2 together represent a C8-C18 non-aromatic dicarboxylic acid group —O(CO)R1R2(CO)O— bridging different platinum centers.

In a third embodiment of bi- or polynuclear platinum complexes of the type [L1L2Pt[O(CO)R1]X]$_n$, L1 and L2 represent the same or different monoolefin ligands; X represents —O(CO)R2; n represents 2, 3, 4, or 5, preferably 2; and —O(CO)R1 and —O(CO)R2 together represent a C8-C18 non-aromatic dicarboxylic acid group —O(CO)R1R2(CO)O— bridging different platinum centers.

Said platinum complexes can be present in the preparation according to the invention in individualized and also in combined form, i.e., alone or also as a mixture of a plurality of different species respectively of the type [L1L2Pt[O(CO)R1]X]$_n$.

L1 and L2 alone represent the same or different, preferably the same monoolefins, or together represent a polyolefinically unsaturated compound L1L2, for example a diolefin or a polyolefin, which can act as a diolefin ligand. The polyolefinically unsaturated compounds L1L2 which can act as diolefin ligands are preferred.

Examples of monoolefins include C2-C18 hydrocarbons having a single olefinically unsaturated double bond. These may be linear compounds, branched compounds, or compounds having cyclic structures. These are preferably pure hydrocarbons; however, the presence of heteroatoms, for example also in the form of functional groups, is also possible. Preferred examples of monoolefins include ethene, propene, and cyclohexene.

Examples of diolefins or, respectively, compounds of the type L1L2 that are capable of acting as diolefin ligands include hydrocarbons such as COD (1,5-cyclooctadiene), NBD (norbornadiene), COT (cyclooctatetraene), and 1,5-hexadiene, in particular COD and NBD. These are preferably pure hydrocarbons; however, the presence of heteroatoms, for example also in the form of functional groups, is also possible.

X can denote bromide, chloride, iodide, or —O(CO)R2; it preferably denotes chloride or —O(CO)R2, in particular —O(CO)R2.

The respective non-aromatic monocarboxylic acid groups —O(CO)R1 and —O(CO)R2 alone represent the same or different C6-C18 or preferably C8-C18 non-aromatic monocarboxylic acid groups, preferably each with the exception of a phenylacetic acid group, or together represent a C8-C18 non-aromatic dicarboxylic acid group of type —O(CO)R1R2(CO)O—. The term "non-aromatic" used in this context excludes purely aromatic monocarboxylic and dicarboxylic acid groups but not araliphatic monocarboxylic and dicarboxylic acid groups whose carboxyl function(s) is/are bound to aliphatic carbon. —O(CO)R1 and also —O(CO)R2 preferably do not denote a phenylacetic acid group. Preferably, —O(CO)R1 and —O(CO)R2 represent the same or different C6-C18 or in particular C8-18 non-aromatic monocarboxylic acid groups, preferably with the respective exception of a phenylacetic acid group; in particular, —O(CO)R1 and —O(CO)R2 preferably represent the same C6-C18 or in particular C8-C18 non-aromatic monocarboxylic acid groups but preferably no phenylacetic acid groups.

Examples of C6-C18 or the preferred C8-C18 non-aromatic monocarboxylic acids comprising the groups —O(CO)R1 or —O(CO)R2 include the isomeric hexanoic acids, including n-hexanoic acid; the isomeric heptanoic acids, including n-heptanoic acid; the isomeric octanoic acids, including n-octanoic acid and 2-ethylhexanoic acid; the isomeric nonanoic acids, including n-nonanoic acid; and the isomeric decanoic acids, including n-decanoic acid, to name just a few examples. Not only linear representatives but also those having branches and/or cyclic structures, such as 2-ethylhexanoic acid, cyclohexanecarboxylic acid, and neodecanoic acid, are included. The R1 and R2 radicals bound in each case to a carboxyl group comprise 5 to 17 and 7 to 17 carbon atoms, respectively; benzyl radicals are preferably excluded in each case.

Examples of C8-C18 non-aromatic dicarboxylic acids of the type HOOCR1R2COOH include correspondingly substituted malonic acids, correspondingly substituted 1,1-cyclobutane dicarboxylic acids, and cyclohexane dicarboxylic acids, to name only a few examples. The structural element —R1R2- bearing two carboxyl groups comprises 6 to 16 carbon atoms.

Preferred examples of platinum complexes (B) include [(COD)Pt[O(CO)R1]$_2$]$_n$ and [(NBD)Pt[O(CO)R1]$_2$]$_n$, wherein n is 1 or 2 and in particular 1, and wherein R1 stands for a C5-C17 or C7-C17 non-aromatic hydrocarbon group, preferably with the exception of a benzyl group.

The platinum complexes [L1L2Pt[O(CO)R1]X]$_n$ can easily be prepared via ligand exchange, in particular without using carboxylic acid salts of silver. The production method includes mixing or, respectively, suspending or emulsifying a two-phase system. One phase comprises a reactant of the type [L1L2PtX$_2$]$_n$, with X selected from bromide, chloride, and iodide, preferably chloride, either as such or in the form of an at least substantially water-immiscible organic solution of such a reactant. Preferred reactants include [L1L2PtCl$_2$]$_n$ with n as a whole number from 1 to 5, in particular with n=1. Examples of suitable at least substantially water-immiscible organic solvents also include oxygen-containing solvents, for example corresponding water-immiscible ketones, esters, and ethers, in addition to aromatics and chlorinated hydrocarbons such as toluene, xylene, di-, tri-, and tetrachloromethane. By contrast, the other phase comprises an aqueous solution of alkali salt (in particular sodium salt or potassium salt) and/or of magnesium salt of a C6-C18 or, respectively, C8-C18 monocarboxylic acid of the type R1COOH, and optionally additionally of the type R2COOH, or corresponding alkali salt and/or magnesium salt of a C8-C18 dicarboxylic acid of the type HOOCR1R2COOH. The selection of the type of carboxylic acid salt(s) depends on the type of platinum complex to be produced or the combination of platinum complexes to be produced. The two phases are intensively mixed, for example by shaking and/or stirring, thereby forming a suspension or an emulsion. For the purpose of maintaining the state of the suspension or emulsion, mixing is carried out for a duration of 0.5 to 24 hours, for example, at a temperature in the range of 20 to 50° C., for example. The ligand exchange takes place in the process, the platinum complex or complexes formed dissolving in the organic phase, while the alkali X salt or $MgX_2$ salt likewise formed dissolves in the aqueous phase. Upon completion of the suspension or emulsification, organic and aqueous phase are separated from one another. The platinum complex or complexes formed can be obtained from the organic phase and, if necessary, subsequently purified by means of conventional methods.

For example, to mention only one specific example, $(COD)Pt[O(CO)CH(C_2H_5)C_4H_9]_2$ can be prepared by jointly emulsifying a solution of $(COD)PtCl_2$ in dichloromethane with an aqueous solution of sodium-2-ethylhexanoate. After completion of emulsification, the saline solution that is thereby formed by ligand exchange can be separated from the dichloromethane phase, and the $(COD)Pt[O(CO)CH(C_2H_5)C_4H_9]_2$ can be isolated from the latter and optionally purified via conventional purification methods. For example, the platinum complex $(COD)Pt[O(CO)CH(C_2H_5)C_4H_9]Cl$ can also be produced analogously if the stoichiometry is selected accordingly.

An important property, in addition to the aforementioned solubility in common organic solvents, is the comparatively low decomposition temperature of the platinum complex or complexes (B), for example already starting at 150° C. to 250° C., often no higher than 200° C. This combination of properties makes it possible to use such platinum complexes as component (B) of the preparation according to the invention for producing platinum layers on substrates; in this type of use, the preparation according to the invention is a coating agent (covering agent), i.e., it is then prepared and usable as a coating agent.

The preparation according to the invention contains 0 to 10% by weight, preferably 0 to 3% by weight of at least one additive (C). Accordingly, the preparation according to the invention can be additive-free or contain up to 10% by weight of at least one additive. Examples of additives include wetting additives, rheological additives, defoamers, deaerators, additives for influencing the surface tension, and odorants.

Preparations according to the invention can be produced by simply mixing components (A), (B), and, if desired, (C). The person skilled in the art selects the quantitative ratio of the components, adapted to the respective intended use and/or to the application method used therein.

The preparations according to the invention can be used to produce platinum layers on substrates, in particular also on temperature-sensitive substrates. The preparations according to the invention can first be used for the production of coating layers (coverings), which can subsequently be subjected to thermal decomposition. During the thermal treatment, the coating layers decompose, forming platinum, i.e., the coating layers are ultimately converted into platinum layers. The invention therefore also relates to a method for producing a platinum layer on a substrate, comprising the following steps:

(1) applying a coating layer of a preparation according to the invention to a substrate, and (2) thermally decomposing the coating layer to form a platinum layer.

The substrates to be provided with the coating layer in step (1) can be substrates that comprise a wide variety of materials. The substrates can comprise only one or even several materials. Examples of materials include, inter alia, glass; carbide substrates such as titanium carbide, molybdenum carbide, tungsten carbide, silicon carbide; nitride substrates such as aluminum nitride, titanium nitride, silicon nitride; boride substrates such as titanium boride, zirconium boride; ceramic substrates including those based on oxidic ceramic and those common as catalyst supports; semiconductor substrates such as silicon substrates; metal; plastic; modified or unmodified polymers of natural origin; carbon substrates; wood; card and paper. The substrates can be provided with the coating layer on inner and/or outer surfaces or on inner and/or outer surface portions.

Known application methods can be used during the production of the coating layer according to step (1).

A first application method is dipping. In this case, the substrate to be provided with the coating layer or ultimately to be provided with the platinum layer is immersed in the preparation according to the invention and then removed again. Preferably, the content of component (A) during dipping is in the range of 30 to 90% by weight of the preparation according to the invention and the content of component (B) is in the range of 10 to 70% by weight.

A second application method is spray application. In this case, the substrate to be provided with the coating layer or ultimately to be provided with the platinum layer is spray-coated with the preparation according to the invention, using a conventional spray-coating tool. Examples of spray-coating tools are pneumatic spray guns, airless spray guns, rotary atomizers, or the like. Preferably, the content of component (A) during spray application is in the range of 50 to 90% by weight of the preparation according to the invention and the content of component (B) is in the range of 10 to 50% by weight.

A third application method is printing. In this case, the substrate to be provided with the coating layer or ultimately to be provided with the platinum layer is printed with the preparation according to the invention. A preferred printing method is inkjet printing. A further preferred printing method is screen printing. Preferably, the content of component (A) during printing is in the range of 50 to 90% by weight of the preparation according to the invention and the content of component (B) is in the range of 10 to 50% by weight.

A fourth application method is the application by means of an application tool saturated with the preparation according to the invention, for example a paintbrush, a brush, a felt, or a cloth. In this case, the preparation according to the invention is transferred from the application tool to the substrate to be provided with the coating layer or ultimately to be provided with the platinum layer. Preferably, the content of component (A) in the case of such an application technique is in the range of 30 to 90% by weight of the preparation according to the invention and the content of component (B) is in the range of 10 to 70% by weight.

The coating layer that is applied from the preparation according to the invention and comprises the at least one platinum complex of type $[L1L2Pt[O(CO)R1]X]_n$ can first be dried and in the process partially or completely freed of the organic solvent before it or the dried residue is subjected to thermal decomposition, forming metallic platinum in the form of a layer. The thermal treatment taking place for the purpose of thermal decomposition comprises heating to an object temperature above the decomposition temperature of the at least one platinum complex. If several different platinum complexes of type $[L1L2Pt[O(CO)R1]X]_n$ are present, the person skilled in the art will select the object temperature above the decomposition temperature of the platinum complex of type (B) having the highest decomposition temperature. For this purpose, for example, heating is generally carried out briefly to an object temperature above the decomposition temperature, for example to an object temperature in the range of 150° C. to 200° C. or 150° C. to 250° C. or higher, for example to 1000° C., for a time period of 1 minute to 30 minutes. Heating can, in particular, take place in a kiln and/or by infrared irradiation. In general, an object temperature is selected to be slightly above the decomposition temperature in question. In general, heating, more precisely maintaining the object temperature, does not take longer than 15 minutes.

It is also advantageous in the production of platinum layers by means of the platinum preparations according to the invention that no preparations containing colloidal platinum or nanoplatinum need to be used, and therefore any risks associated with them can be avoided. Moreover, in the second and third of the aforementioned application methods, clogging of the application tools, more precisely, clogging of fine openings or nozzles of spray application tools or inkjet nozzles can be avoided through the use of the preparation according to the invention; and finally the question of colloidal platinum or nanoplatinum drying on or aggregating does not arise here.

The platinum layers thus obtainable are characterized by high metallic luster comparable to a mirror, provided one works with substrates having smooth surfaces that are not too rough; the platinum layers are homogeneous in terms of a smooth, non-granular outer surface. The thickness of such platinum layers obtainable by the method according to the invention may, for example, be in the range of 50 nm to 5 μm, and the platinum layers may have an areal nature with or without desired discontinuities within the area, or may have a desired pattern or design. As is apparent from the aforementioned examples of substrates, the platinum layers can even be produced on temperature-sensitive substrates, i.e., for example, on substrates that are not temperature-stable above 200° C.; for example, they can be temperature-sensitive polymer substrates, for example those based on polyolefins or polyesters.

EXAMPLES

Example 1 (Provision of a Glass Slide with a Platinum Layer)

A solution of 65 mmol $(COD)PtCl_2$ in 100 ml dichloromethane was stirred, and a solution of 260 mmol sodium-2-isodecanoate in 500 ml water was added. The two-phase mixture was emulsified for 24 h at 20° C. by vigorous stirring. The dichloromethane phase turned yellow in the process.

The dichloromethane phase was separated, and the solvent was distilled off. The viscous, yellow residue was absorbed into 150 ml petroleum benzine (40-60), and the solution was dried with magnesium sulfate and filtered. The petroleum benzine was then completely distilled off. A viscous yellow residue of $(COD)Pt[O(CO)(CH_2)_5 C(CH_3)_3]_2$ remained.

10 g of the yellow residue were dissolved in 20 g of a solvent/additive mixture (50% by weight of ethanol, 49.9% by weight of propylene glycol monopropyl ether, 0.1% by weight of BYK-333 (surface additive from BYK). The solution containing 10% by weight platinum was sprayed onto a glass slide by means of an airbrush spray gun. The coated glass slide was heated in a laboratory kiln to an object temperature of 200° C. and kept at this temperature for 15 minutes. A glossy electrically conductive layer of platinum had formed on the slide.

Examples 2a to 2d (Provision of Aluminum Oxide Plates with a Platinum Layer)

2a: An unglazed plate of aluminum oxide (50 mm×50 mm) was immersed in the solution from example 1 and, after being removed, was heated in a laboratory kiln to an object temperature of 200° C. and kept at this temperature for 15 minutes. A glossy electrically conductive layer of platinum had formed on the plate.

2b: Experiment 2a was repeated at an object temperature of 900° C., obtaining a comparable result.

2c and 2d: Experiments 2a and 2b were repeated with a glazed plate of aluminum oxide, giving comparable results but here, in contrast to the result of experiments 2a and 2b, in the form of reflective electrically conductive layers of platinum.

Example 3 (Provision of a Polyurethane Tube with a Platinum Layer)

A 5 mm thick tube made of polyurethane was drawn three times in succession through a piece of felt impregnated with the solution from example 1. The tube thus coated was heated in a laboratory kiln to an object temperature of 175° C. and kept at this temperature for 5 minutes. A glossy electrically conductive layer of platinum had formed on the tube.

Example 4 (Provision of a Polyimide Film with a Patterned Platinum Layer)

A Kapton® film (polyimide) was printed with the solution from example 1 with the aid of an inkjet printer at a resolution of 1270 dpi in a meander design. The film thus printed was heated in a laboratory kiln to an object temperature of 200° C. and kept at this temperature for 5 minutes. A glossy electrically conductive layer of platinum in the shape of the meander design, having a width of the conductor tracks of 2.5 mm, had formed on the film.

Example 5 (Provision of a Glass Slide with a Platinum Layer)

Analogously to example 1, 32.5 mmol $(COD)PtCl_2$ in 100 ml dichloromethane were reacted with 130 mmol sodium cyclohexanoate in 200 ml water. This gave a yellow residue of $(COD)Pt[O(CO)C_6H_{11}]_2$.

2 g of the yellow residue were dissolved in 4.86 g of dipropylene glycol monopropyl ether. A glass slide was immersed in this solution containing 10% by weight platinum and, after being removed, was heated in a laboratory kiln to an object temperature of 200° C. and kept at this temperature for 15 minutes. A glossy electrically conductive layer of platinum had formed on the slide.

Example 6 (Provision of a Polyimide Film with a Platinum Layer)

Analogously to example 1, 65 mmol (COD)PtCl$_2$ in 100 ml dichloromethane were reacted with 260 mmol sodium-2-ethylhexanoate in 500 ml water. A yellow residue of (COD)Pt[O(CO)CH(C$_2$H$_5$)C$_4$H$_9$]$_2$ was obtained.

10 g of the yellow residue were dissolved in a mixture of 15 g of propylene glycol monopropyl ether and 15 g of ethanol. A 10×40 mm strip of a Kapton® film was immersed in this solution containing 8.2% by weight of platinum and, after being removed, was heated in a laboratory kiln to an object temperature of 200° C. and kept at this temperature for 3 minutes. A glossy electrically conductive layer of platinum had formed on the film.

Example 7 (Provision of a Glazed Aluminum Oxide Plate with a Platinum Layer)

A glazed plate of aluminum oxide was immersed in the solution from example 6 and, after being removed, was heated in a laboratory kiln to an object temperature of 200° C. and kept at this temperature for 5 minutes. A glossy electrically conductive layer of platinum had formed on the plate.

Example 8 (Provision of a Polyimide Film with a Platinum Layer)

Analogous to Example 1, 27.3 mmol (NBD)PtCl$_2$ in 100 ml dichloromethane was reacted with 110 mmol sodium-2-ethylhexanoate in 100 ml water. A yellow residue of (NBD)Pt[O(CO)CH(C$_2$H$_5$)C$_4$H$_9$]$_2$ was obtained, which was further processed analogously to example 6 to obtain a Kapton® film provided with a glossy electrically conductive layer of platinum.

The invention claimed is:

1. A preparation consisting of:
   (A) 30 to 90% by weight of at least one organic solvent;
   (B) 10 to 70% by weight of at least one platinum complex of the type [L1L2Pt[O(CO)R1]X]$_n$,
   wherein L1 and L2 represent the same or different monoolefin ligands, or together represent a compound L1L2 acting as a diolefin ligand,
   wherein X is selected from bromide, chloride, iodide, and —O(CO)R2,
   wherein —(CO)R1 and —O(CO)R2 represent the same or different C6-C18 or C8-C18 non-aromatic monocarboxylic acid groups, or together represent a C8-C18 non-aromatic dicarboxylic acid group —O(CO)R1R2(CO)O—,
   wherein they are mononuclear platinum complexes with n=1, or wherein, if L1L2 and/or —O(CO)R1R2(CO)O— are present, they may be polynuclear platinum complexes with a whole number n>1, and
   (C) 0 to 10% by weight of at least one additive.

2. The preparation according to claim 1, wherein L1L2 represents a compound acting as a diolefin ligand, wherein X is selected from bromide, chloride, iodide, and —O(CO)R2,
   wherein —O(CO)R1 and —O(CO)R2 represent the same or different C6-C18 or C8-C18 non-aromatic monocarboxylic acid groups, and
   wherein they are mononuclear platinum complexes with n=1, or polynuclear platinum complexes with a whole number n>1.

3. The preparation according to claim 1, wherein whole number n>1 is in the range of 2 to 5.

4. The preparation according to claim 1 in the form of a non-colloidal organic solution.

5. The preparation according to claim 1, having a platinum content originating from the at least one platinum complex in the range of 2.5 to 25% by weight.

6. The preparation according to claim 1, wherein the at least one platinum complex has the formula [(COD)Pt[O(CO)R1]$_2$]$_n$ or [(NBD)Pt[O(CO)R1]$_2$]$_n$, wherein n is 1 or 2, and wherein R1 stands for a C5-C17 or C7-C17 non-aromatic hydrocarbon group.

7. The preparation according to claim 1, wherein the decomposition temperature of the at least one platinum complex is in the range of 150 to 200 or 150 to 250° C.

8. The preparation according to claim 1, wherein the at least one additive (C) is selected from the group consisting of wetting additives, rheological additives, defoamers, deaerators, additives for influencing the surface tension and odorants.

9. A method for producing a platinum layer on a substrate, comprising the steps of:
   (1) applying a coating layer of a preparation according to claim 1 to a substrate, and
   (2) thermally decomposing the coating layer to form a platinum layer.

10. The method according to claim 9, wherein the substrate comprises one or more materials selected from the group consisting of glass, ceramic, semiconductor substrates, metal, plastic, modified or unmodified polymers of natural origin, carbon substrates, card and paper.

11. The method according to claim 9, wherein the substrate is provided with the coating layer on inner and/or outer surfaces or on inner and/or outer surface portions.

12. The method according to claim 9, wherein the application method used to produce the coating layer is selected from the group consisting of dipping, spray application, printing, application by means of paintbrush, application by means of brush, application by means of felt, and application by means of cloth.

13. The method according to claim 9, wherein the coating layer applied in step (1) is initially dried and in the process partially or completely freed of the organic solvent before it is subjected to thermal decomposition in step (2).

14. The method according to claim 9, wherein the thermal decomposition according to step (2) takes place by thermal treatment, which comprises heating to an object temperature above the decomposition temperature of the at least one platinum complex.

15. The method according to claim 14, wherein the heating to the object temperature takes place in a kiln and/or by infrared irradiation.

16. The method according to claim 9, wherein the platinum layer is 50 nm to 5 μm thick.

* * * * *